(12) United States Patent
Thompson et al.

(10) Patent No.: US 8,007,996 B2
(45) Date of Patent: Aug. 30, 2011

(54) METHODS TO IDENTIFY PROTEIN ARGININE DEIMINASE 4 INHIBITORS

(75) Inventors: Paul R. Thompson, Columbia, SC (US); Bryan Knuckley, West Columbia, SC (US)

(73) Assignee: University of South Carolina, Columbia, SC (US)

( * ) Notice: Subject to any disclaimer, the term of this patent is extended or adjusted under 35 U.S.C. 154(b) by 229 days.

(21) Appl. No.: 12/262,436

(22) Filed: Oct. 31, 2008

(65) Prior Publication Data

US 2009/0162877 A1    Jun. 25, 2009

Related U.S. Application Data

(60) Provisional application No. 61/008,598, filed on Dec. 20, 2007.

(51) Int. Cl.
*C12Q 1/00*        (2006.01)

(52) U.S. Cl. ............................................. 435/4

(58) Field of Classification Search ...................... 435/4
See application file for complete search history.

(56) References Cited

OTHER PUBLICATIONS

Luo et al. "Activity-based protein profiling reagents for protein arginine deiminase 4 (PAD4): synthesis and in vitro evaluation of a fluorescently labeled probe", J. Am. Chem. Soc. 2006, 128:14468-14469.*

* cited by examiner

*Primary Examiner* — Sue Liu
*Assistant Examiner* — Bin Shen
(74) *Attorney, Agent, or Firm* — Dority & Manning, P.A.

(57) ABSTRACT

In accordance with one embodiment of the present disclosure, a method to identify a protein arginine deiminase 4 inhibitor is disclosed. The method includes performing a competitive assay in which a potential inhibitor compound competes with rhodamine-conjugated fluoroamidine to bind to protein arginine deiminase 4. Fluorescence is measured to determine an estimate of the amount of fluorescent protein arginine deiminase 4 that is present in the assay.

4 Claims, 3 Drawing Sheets

METHODS TO IDENTIFY PROTEIN ARGININE DEIMINASE 4 INHIBITORS

CROSS REFERENCE TO RELATED APPLICATION

The present application is based on and claims priority to U.S. Provisional Application Ser. No. 61/008,598 having a filing date of Dec. 20, 2007, which is incorporated by reference herein.

BACKGROUND

Rheumatoid arthritis (RA) is a chronic progressive autoimmune disorder that ultimately leads to the destruction of the cartilage surrounding the joint. It is the second most common type of arthritis with symptoms first appearing in patients between 40 and 60 years of age. Current RA therapeutics can be classified into 3 groups: Non-Steroidal Anti-Inflammatory Drugs (NSAIDs), corticosteroids, and Disease Modifying Anti-Rheumatic Drug's (DMARDs). The NSAIDs (e.g. aspirin, ibuprofen, naproxen) and corticosteroids encompass a large group of clinically effective compounds whose mode of action is well established—these compounds relieve pain and reduce inflammation by preventing prostaglandin synthesis through inhibition of cyclooxygenase 2 and the production of arachidonic acid, respectively. The DMARDs are an equally large group of therapeutics that includes both chemical (i.e., small molecules) and biological agents, e.g. antibody-based therapies. Examples of biological DMARDs include drugs such as etanercept, infliximab, and tocilizumab, which are therapeutically effective because they reduce the levels of inflammatory cytokines. Examples of chemical DMARDs include methotrexate, minocycline, and leflunomide. Interestingly, and in contrast to the well established modes of action of the NSAIDs, corticosteroids, and biological DMARDs, the molecular mechanisms by which the chemical DMARDs function as RA therapeutics are incompletely understood in several cases, e.g. minocycine.

Protein Arginine Deiminase 4 (PAD4), which catalyzes the conversion of peptidyl-arginine to peptidyl-citrulline, is widely believed to play a causative role in RA disease onset and progression because RA-associated mutations in the PAD4 gene have been identified in a variety of populations and RA patients produce autoantibodies that recognize citrulline-containing proteins. Interestingly, the anti-citrulline autoantibodies are considered to be the most specific diagnostic marker of this disease and there is a direct correlation between the levels of citrullinated proteins and disease severity, especially in the formative stages of RA. In total, the serological and genetic data suggest that PAD4 activity is dysregulated in RA, thereby suggesting this enzyme as a target for the development of a novel RA therapeutic.

While the development of the two most potent PAD4 inhibitors described to date have been reported, one or more of the aforementioned chemical DMARDs could inhibit this enzyme and thereby offer an explanation for their clinical efficacy. However, the standard PAD4 assay, which measures citrulline formation, is not readily amenable to high or even low throughput screens because it suffers from several limitations, including the fact that it requires the use of strong acids, toxic reagents, and high temperatures to convert the ureido group into a chromophore that absorbs light at 540 nm. Additionally, a number of compounds interfere with this assay, suggesting that potential inhibitors may be missed during the screening process. Therefore, a new inhibitor screen that remedies such shortcomings would be particularly beneficial.

SUMMARY

In accordance with one embodiment of the present disclosure, a method to identify a protein arginine deiminase 4 inhibitor is disclosed. The method includes performing a competitive assay in which a potential inhibitor compound competes with rhodamine-conjugated fluoroamidine to bind to protein arginine deiminase 4. Fluorescence is measured to determine an estimate of the amount of fluorescent protein arginine deiminase 4 that is present in the assay.

In another embodiment of the present disclosure, a kit for identifying a protein arginine deiminase 4 inhibitor is disclosed. The kit includes rhodamine-conjugated fluoroamidine and an assay device.

Other features and aspects of the present disclosure are discussed in greater detail below.

BRIEF DESCRIPTION OF THE DRAWINGS

A full and enabling disclosure, including the best mode thereof, directed to one of ordinary skill in the art, is set forth more particularly in the remainder of the specification, which makes reference to the appended figures in which.

Figure 1:
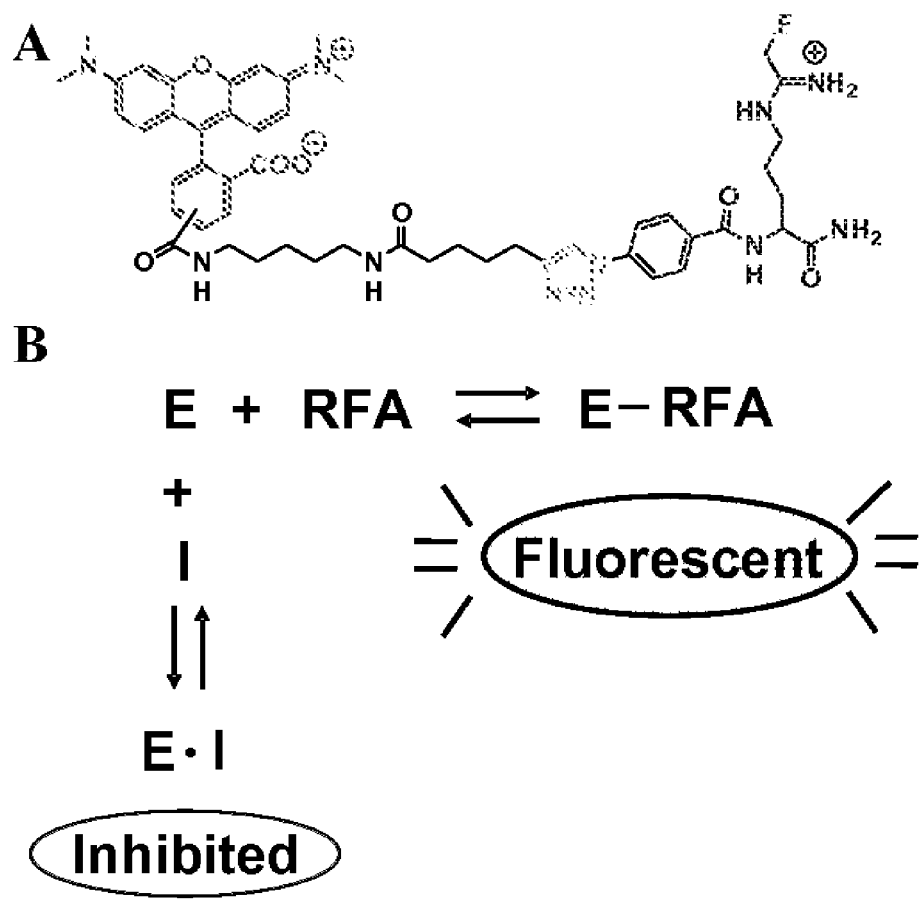
FIG. 1A illustrates the structure of Rhodamine-conjugated Fluoro-Amidine (RFA) in accordance with the present disclosure.
FIG. 1B illustrates that RFA can covalently modify the active site of the enzyme (E), rendering the protein fluorescent, or the inhibitor (I) can bind to the enzyme and inhibit this process in accordance with the present disclosure.

Repeat use of reference characters in the present specification and drawings is intended to represent same or analogous features or elements of the disclosure.

DETAILED DESCRIPTION

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

The present disclosure is generally directed to a new inhibitor screen for PAD4. The novel inhibitor screen was developed to take advantage of a PAD4-targeted Activity-Based Protein Profiling (ABPP) reagent that is denoted Rhodamine-tagged F-amidine (RFA). Referring to FIG. 1, RFA links a novel mechanism-based inactivator to a fluorophore and has previously been used to label purified PAD4 as well as enzyme present in cell extracts. The screen described herein is essentially a competition assay in which library components compete with RFA for binding and covalent modification of PAD4. While similar to competitive ABPP strategies for identifying inhibitors in complex proteomes, the screening assay of the present disclosure uses competitive ABPP to overcome the limitations of current assays in a system with purified proteins. The present disclosure describes an ABPP-based screen and its utility in identifying PAD4 inhibitors. Significantly, streptomycin, chlortetracycline, and minocycline are all identified as PAD4 inhibitors; and while the potency of these compounds is relatively weak, their identification indicates several new chemical scaffolds that can be exploited in the design of future PAD4 inhibitors.

The development of rapid and accurate detection methods of enzyme activity is vital for the discovery of enzyme inhibitors via high-throughput screening of compound libraries. However as described above with regard to PAD4, current assays are not readily amenable to high-throughput screens. Therefore, the present disclosure describes a competition assay in which an individual member of a library of compounds competes with the PAD4-targeted ABPP RFA for binding to PAD4.

Very generally, potential inhibitor compounds are incubated individually with PAD4 in the presence of RFA for 30 min at 37° C.; at which point the reactions are quenched with SDS-PAGE loading dye and the mixtures are run on an SDS-PAGE gel. The amount of fluorescent PAD4 can then be quantified using a molecular imaging system. PAD4 inhibitors are readily identified by a decrease in fluorescence intensity.

Figure 2A:
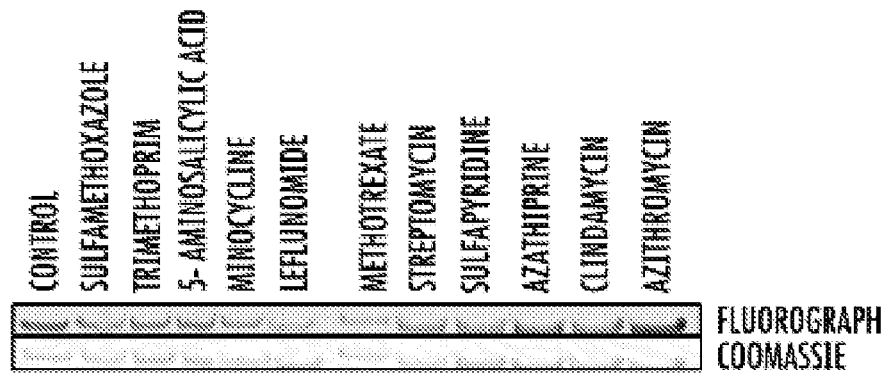
FIG. 2A illustrates a fluorescent image of SDS-PAGE gels (top) in which PAD4 was treated with RFA (10 µM final) in the absence and presence of the indicated DMARDs with the coomassie stained SDS-PAGE gel is shown (bottom) to demonstrate equal protein loading.
Figure 2B:
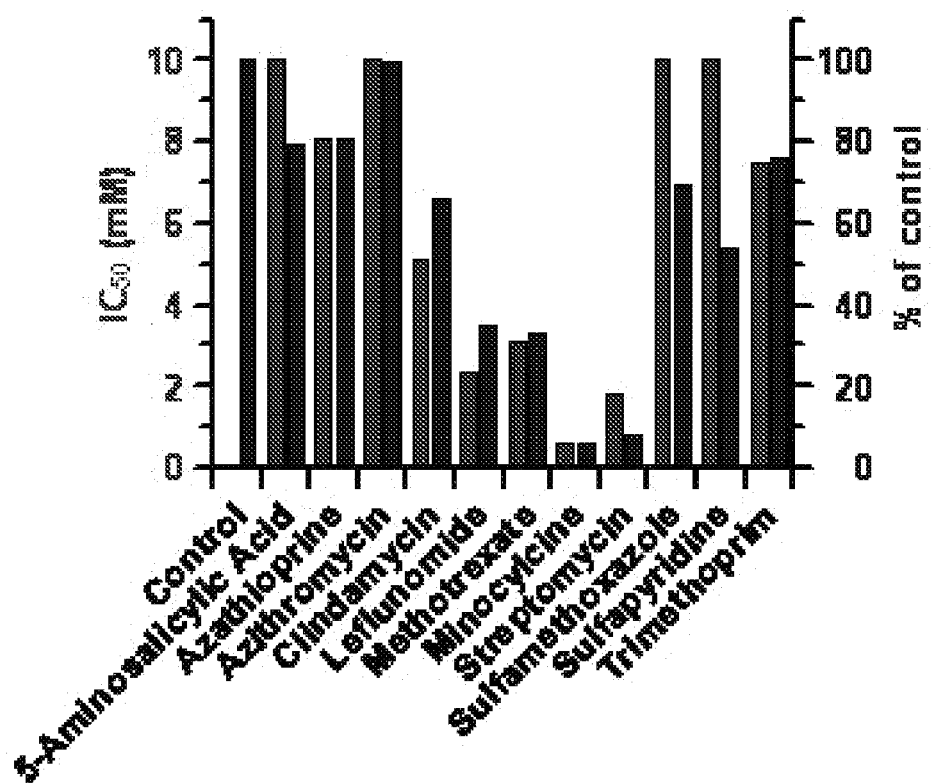
FIG. 2B illustrates a plot of the $IC_{50}$ values for the various DMARDs compared to the fluorescence quantified as a percent of the control.

Using an assay in accordance with the present disclosure, 10 DMARDs (sulfamethoxazole, trimethoprim, 5-aminosalicylic acid, minocycline, leflunomide, methotrexate, sulfapyridine, azathioprine, clindamycin, azithromycin) were rapidly screened as well as streptomycin for their ability to inhibit PAD4. Streptomycin was tested because this antibiotic contains two guanidinium groups that could potentially mimic the guanidinium group of an Arg residue and thereby act as either a substrate or inhibitor of PAD4. Referring to FIGS. 2A and 2B, the results identified minocycline and streptomycin as PAD4 inhibitors, as can be seen by the strong decrease in fluorescence intensity in the lanes corresponding to these two compounds. To help validate this novel ABPP-based inhibitory screen, the $IC_{50}$ values for all of the aforementioned compounds were determined. The results, which are depicted in Table 1 and FIG. 2B (blue bars represent the fluorescence intensity as a percent of control, red bars represent the $IC_{50}$ of individual library components) are consistent with the standard ABPP-based assay. For example, the $IC_{50}$'s of 5-aminosalicylic acid, azathioprine, azithromycin, sulfamethoxazole, sulfapyridine, and trimethoprim were all above 7.5 mM in the standard assay and there was little to no decrease in the fluorescence of PAD4 when these compounds were incubated with the enzyme and RFA. In contrast, the compounds that decreased the intensity of PAD4 fluorescence the most, i.e. streptomycin and minocycline, were also the most potent compounds on the standard assay, with $IC_{50}$ values of 1.8 mM and 0.62 mM, respectively. Intermediate effects on PAD4 fluorescence were observed for the remaining compounds (i.e. clindamycin, leflunomide, and methotrexate), consistent with their $IC_{50}$'s. It should be noted that streptomycin was not deiminated by PAD4 despite the fact that this compound possesses two guanidinium groups.

The fact that minocycline was the most potent inhibitor identified in this screen indicated that other tetracycline derivatives inhibit PAD4 with equal or greater potency. Therefore, $IC_{50}$ values for tetracycline, doxycycline, and chlortetracycline were determined. The results of these studies, as illustrated in Table 2, indicate that chlortetracycline ($IC_{50}$=100 μM) is significantly more potent (5-fold) than minocycline ($IC_{50}$=620 μM). Chlortetracycline differs from minocycline by the addition of a hydroxyl and methyl group at position 6 along with a chloro group replacing the dimethylamine moiety at position 7.

Figure 3:
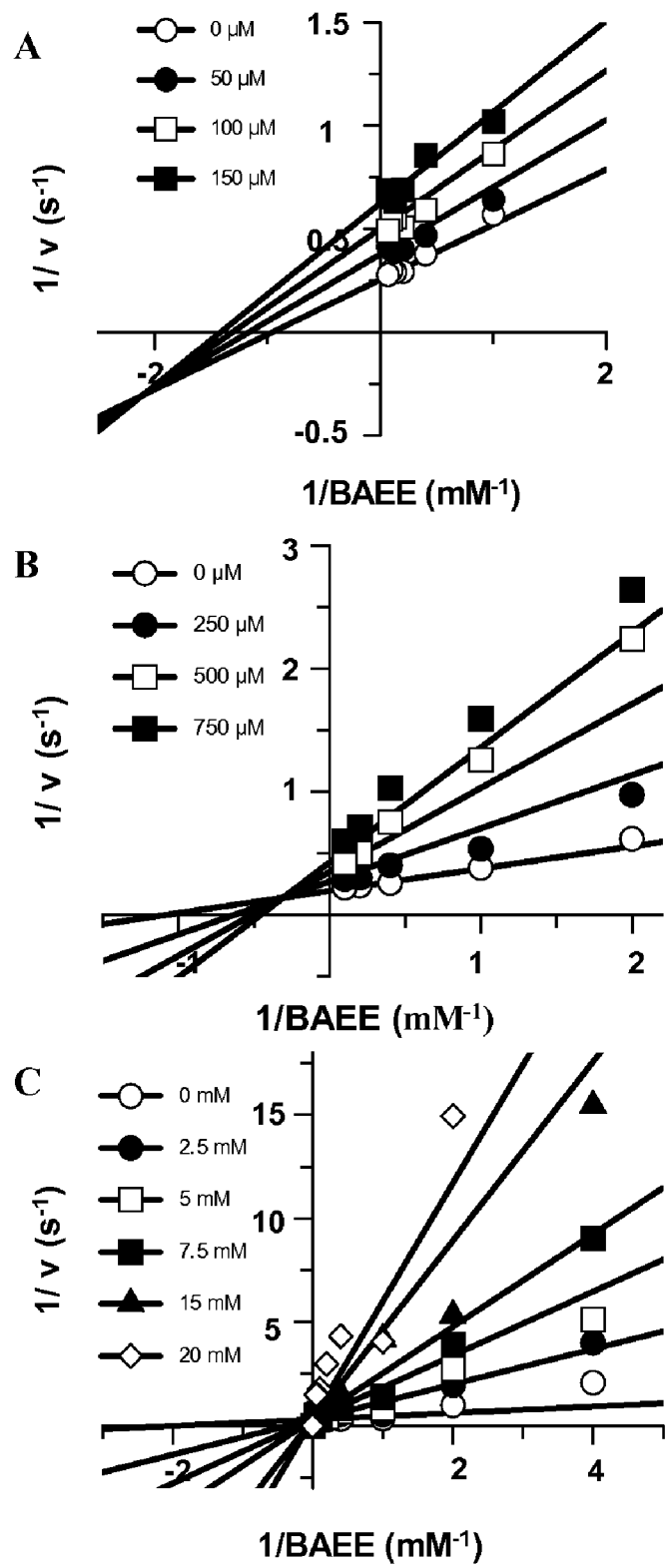
FIG. 3A illustrates a mixed inhibition plot for chlortetracycline.
FIG. 3B illustrates the mixed inhibition plot for minocycline.
FIG. 3C illustrates the competitive inhibition plot for streptomycin.

The kinetic mechanism by which chlortetracycline, minocycline, and streptomycin inhibit PAD4 activity was evaluated in accordance with the present disclosure. PAD4 activity was measured as a function of substrate concentration in the absence and presence of increasing concentrations of each inhibitor. Note that in all cases product formation was linear with respect to time, indicating that these compounds are reversible PAD4 inhibitors. Referring to FIG. 3A, Lineweaver-Burk plots (1/v versus 1/[S]) of the chlortetracycline inhibition data are consistent with mixed inhibition. The $K_{ii}$ and $K_{is}$ values are 0.11±0.01 mM and 0.54±0.53 mM, respectively. Turning to FIG. 3B, minocycline was also a mixed type inhibitor with $K_{ii}$ and $K_{is}$ values of 0.63±0.15 mM and 0.18±0.06 mM, respectively. Lastly, FIG. 3C illustrates streptomycin is a competitive inhibitor of PAD4, as evidenced by the family of lines intersecting on the 1/v-axis (FIG. 3C), with a $K_{is}$ value equal to 0.56±0.17 mM.

While the molecular mechanisms linking a dysregulated PAD4 activity to RA are incompletely defined, an abundance of evidence strongly suggests that non-specific Arg deimination causes the production of citrulline-containing epitopes that the immune system recognizes as foreign, leading first to a break in tolerance, and then ultimately resulting in RA disease onset and progression. Because PAD4 inhibitors would decrease the levels of citrulline-containing proteins, this enzyme has recently emerged as a new target for the development of a novel RA therapeutic. The need for new RA drugs is highlighted by the fact that current therapeutic regimens, e.g. the NSAIDs and corticosteroids, are focused primarily on alleviating the pain and inflammation associated with this autoimmune disorder and not an underlying cause of the disease.

The well established utility of high-throughput screening efforts in drug discovery indicates that a large library of compounds can be screened to identify novel PAD4 inhibitors and/or pharmacophores. To overcome the aforementioned limitations of the standard PAD activity assay, the novel and straightforward methods for screening large libraries of compounds for PAD4 inhibitors, as described herein, was developed. The assays described herein are based on an ABPP that selectively modifies an active site Cys in PAD4, rendering the enzyme fluorescent. 10 DMARDs were screened for their ability to inhibit PAD4. These FDA approved drugs were chosen for the initial screen described herein because they have shown efficacy in ameliorating RA disease progression and their value as RA therapeutics is due in part to their ability to inhibit PAD4 activity.

Using this ABPP-based assay, minocycline and streptomycin were rapidly identified as PAD4 inhibitors. Their ability to act as PAD4 inhibitors was confirmed by comparing the decrease in fluorescence intensity to the $IC_{50}$ values determined using the standard PAD4 assay. The ABBP-based assay was further validated by determining the $IC_{50}$ values for the remaining compounds present in the screen and those values are consistent with the relative change in fluorescence intensity observed for all of the compounds tested. Because minocycline is a member of the tetracycline family of antibiotics, the inhibitory properties of chlortetracycline, tetracycline, and doxycycline were evaluated and this secondary screen identified chlortetracycline as a third PAD4 inhibitor.

Kinetic studies with chlortetracycline, minocycline, and streptomycin—the three most potent inhibitors identified in the primary and secondary screens undertaken—revealed that chlortetracycline and minocycline are mixed inhibitors whereas streptomycin is a competitive inhibitor. These results are consistent with the notion that streptomycin binds within the active site of PAD4, or alternatively in close proximity to it—the two guanidinium groups on streptomycin are likely important for this interaction. In contrast, the fact that minocycline and chlortetracycline are mixed inhibitors demonstrates that these two compounds bind to a site distal from the active site.

The fact that minocycline and other tetracycline compounds are PAD4 inhibitors is of note because the use of these compounds as DMARDs has been in question due to conflicting reports on their efficacy as RA therapeutics. While these compounds function as RA therapeutics by impairing neutrophil chemotaxis and acting as anti-inflammatory agents, their efficacy is due in part to their ability to inhibit PAD4; along with their ability to inhibit a wide range of enzymes, including collagenase, poly(ADP-ribose) polymerase-1 (PARP-1), and several cysteine proteinases; contributes to their efficacy as an RA therapeutic.

In summary, a novel ABPP-based assay is described herein that overcomes the limitations of the standard PAD4 assay by eliminating the need for strong acids, high temperatures, and toxic compounds. While the use of a gel-based detection screen is described herein, the methodology can also be adapted to a solution-based system using a 96-well multiscreen filter plate; thereby facilitating the screening of large libraries of compounds for PAD4 inhibitors. Finally, the tetracycline and streptomycin structures identified with this screen represent important chemical scaffolds that can serve as a starting point for the synthesis of future PAD4 inhibitors.

The present disclosure can be better understood with reference to the following examples.

EXAMPLE

Azathioprine, azithromycin, clindamycin, minocyclcine, streptomycin, sulfamethoxazole, 5-aminosalicylic acid, sulfapyridine, trimethoprim, tetracycline, dithiothreitol (DTT) and Benzoyl L-arginine ethyl ester (BAEE) were acquired from Sigma-Aldrich (St. Louis, Mo.). Methotrexate was purchased from Fluka. Leflunomide was purchased from Toronto Research Chemicals (Ontario, Canada). Chlortetracycline and doxycycline were purchased from Alexis Biochemicals (San Diego, Calif.). RFA can be synthesized by any suitable method as would be known in the art. Recombinant human PAD4 was expressed and purified as would be known in the art.

Inhibitor Screen

The compounds tested in the screen and their chemical structures are listed in Table 1. RFA (10 µM final) and a particular compound from the library (2.5 mM final) were pre-incubated in Screening Buffer (500 µM TCEP, 10 mM $CaCl_2$, 100 mM HEPES 7.6, 50 mM NaCl) for 10 min at 37° C. PAD4 (2 µM final) was then added to this mixture and incubated for 30 min at 37° C. The reaction was quenched with 6×SDS-PAGE Dye, incubated at 95° C. for 10 min, and then loaded onto a 12% SDS-PAGE gel. After electrophoresis, the gel was placed in destaining buffer (10% glacial acetic acid, 45% methanol, 45% $ddH_2O$) until the fluorescence was measured using a fluorescence based molecular imaging station (Kodak Image Station 2000MM; excitation at 535 nm, emission at 600 nm). The protein gel was then stained and destained to ensure equal protein loading. A sample without a potential inhibitor was used as a control.

$IC_{50}$ Studies $IC_{50}$ values were determined by pre-incubating various amounts of the potential inhibitor in Reaction Buffer (10 mM $CaCl_2$, 2 mM DTT, 50 mM NaCl, 100 mM Tris HCl pH 7.6) and 0.2 µM PAD4 at 37° C. After 15 minutes, Benzoyl Arginine Ethyl Ester (BAEE; 1 mM final; 0.74×$K_m$) was added and the reaction was allowed to proceed for 15 minutes (60 µL total volume). Reactions were quenched by flash freezing in liquid $N_2$. The amount of Cit produced was then quantified according to methods known in the art. $IC_{50}$ values were determined by fitting the data to equation 1, $$\text{FracionalActivity} = 1/(1 + [I]/IC_{50}) \quad (1)$$

using GraFit version 5.0.11.

Inhibition Studies.

Inhibition constants were determined for minocycline, chlortetracycline, and streptomycin using standard kinetic analyses. Briefly, the compounds were incubated in Reaction Buffer containing various concentrations of BAEE (0-20 mM) for 10 minutes at 37° C. PAD4 (0.2 µM) was then added to initiate the reaction and allowed to proceed for 6 additional minutes. Reactions were then quenched by flash freezing in liquid $N_2$ and the amount of Cit produced was quantified. The data obtained for streptomycin, minocycline and chlortetracycline were fit to equations 2 and 3, $$\frac{1}{v_o} = \frac{\left(1+\frac{[I]}{K_{ii}}\right)K_m}{V_{max}}\left(\frac{1}{[S]}\right) + \frac{\left(1+\frac{[I]}{K_{is}}\right)}{V_{max}} \quad (2)$$

$$\frac{1}{v_o} = \frac{\left(1+\frac{[I]}{K_{ii}}\right)K_m}{V_{max}}\frac{1}{[S]} + \frac{1}{V_{max}} \quad (3)$$

using GraFit version 5.0.11.

In the interests of brevity and conciseness, any ranges of values set forth in this specification are to be construed as written description support for claims reciting any sub-ranges having endpoints which are whole number values within the specified range in question. By way of a hypothetical illustrative example, a disclosure in this specification of a range of 1-5 shall be considered to support claims to any of the following sub-ranges: 1-4; 1-3; 1-2; 2-5; 2-4; 2-3; 3-5; 3-4; and 4-5.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only, and is not intended to limit the disclosure so further described in such appended claims.

TABLE 1

Structures and IC$_{50}$'s of DMARDs tested in this study.

| Compound | Structure | IC$_{50}^{a}$ (mM) |
|---|---|---|
| 5-Amino-salicylic Acid | 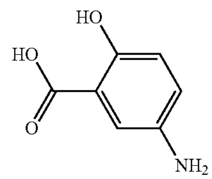 | >10 |
| Azathioprine | 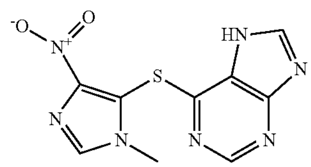 | 8.1 ± 0.8 |
| Azithromycin | 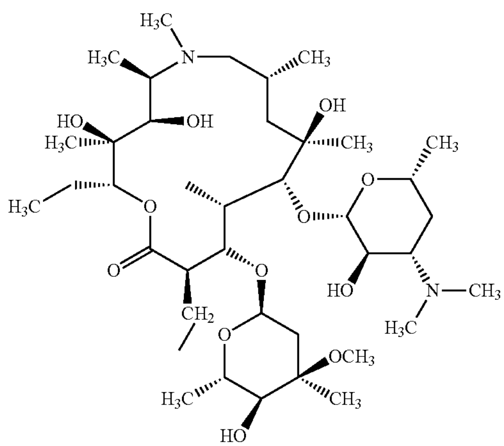 | >10 |
| Clindamycin | 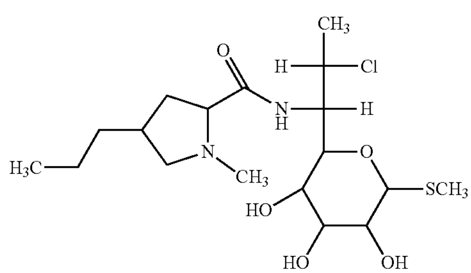 | 5.1 ± 0.3 |
| Leflunomide | 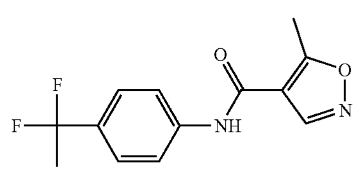 | 2.4 ± 0.8 |
| Methotrexate | 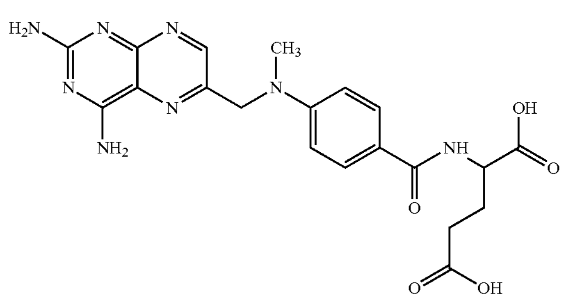 | >10 |

TABLE 1-continued

Structures and IC$_{50}$'s of DMARDs tested in this study.

| Compound | Structure | IC$_{50}$[a] (mM) |
|---|---|---|
| Streptomycin | 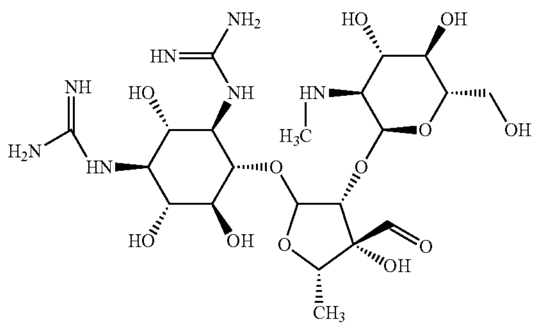 | 1.8 ± 0.3 |
| Sulfamethox-azole | 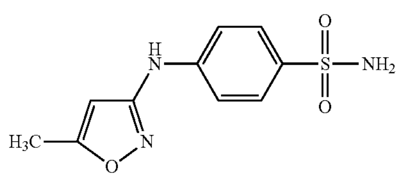 | >10 |
| Sulfapyridine | 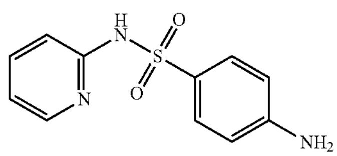 | >10 |
| Trimethoprim | 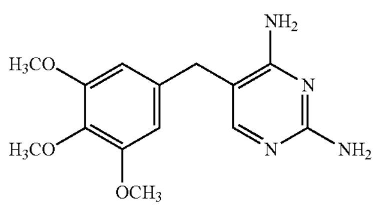 | 7.5 ± 0.2 |

[a]IC$_{50}$ values for the DMARDs screened determined using 1 mM BAEE

TABLE 2

Structures and IC$_{50}$'s of tetracycline derivatives tested in this study.

| Compound | Structure | IC$_{50}$[a] (mM) |
|---|---|---|
| Minocycline | 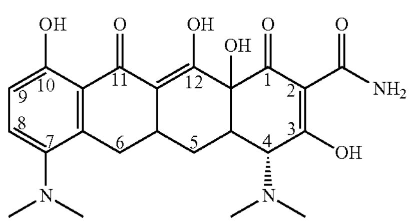 | 0.62 ± 0.01 |
| Chlortetracycline | 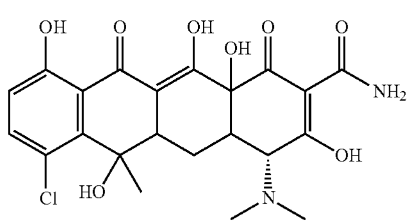 | 0.55 ± 0.07 |

TABLE 2-continued

Structures and IC$_{50}$'s of tetracycline derivatives tested in this study.

| Compound | Structure | IC$_{50}^{a}$ (mM) |
|---|---|---|
| Tetracycline | 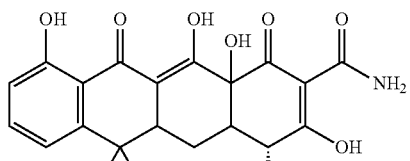 | 0.1 ± 0.01 |
| Doxycycline | 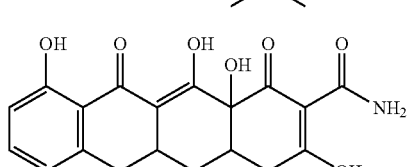 | 0.86 ± 0.08 |

$^{a}$IC$_{50}$ values for the tetracycline derivatives using 1 mM BAEE

What is claimed is:

1. A method to identify a protein arginine deiminase 4 inhibitor comprising:
   performing a control assay in which rhodamine-conjugated fluoroamidine binds to protein arginine deiminase 4;
   measuring fluorescence to determine an estimate of the amount of fluorescent protein arginine deiminase 4 that is present in the control assay;
   performing a competitive assay in which a potential inhibitor compound competes with rhodamine-conjugated fluoroamidine to bind to protein arginine deiminase 4; and
   measuring fluorescence to determine an estimate of the amount of fluorescent protein arginine deiminase 4 that is present in the competitive assay;
   determining if the potential inhibitor compound is likely to act as an inhibitor of protein arginine deiminase 4 based on the estimate of the amount of fluorescent protein arginine deiminase 4 that is present in the competitive assay, wherein a decrease in fluorescence in the competitive assay when compared to the control assay is indicative that the potential inhibitor compound is a protein arginine deiminase 4 inhibitor.

2. A method as in claim 1, wherein no decrease in the fluorescence in the competitive assay when compared to the control assay is indicative that the potential inhibitor compound is not a protein arginine deiminase 4 inhibitor.

3. A method as in claim 1, wherein the potential inhibitor compound comprises a disease modifying anti-rheumatic drug.

4. A method as in claim 3, wherein the potential inhibitor compound comprises a chemical disease modifying anti-rheumatic drug.

* * * * *